(12) United States Patent
Dooney, Jr. et al.

(10) Patent No.: US 9,113,859 B2
(45) Date of Patent: Aug. 25, 2015

(54) SUTURE ANCHOR EYELET WITH SUTURE LOADER

(75) Inventors: Thomas Dooney, Jr., Naples, FL (US); John A. Sodeika, Naples, FL (US)

(73) Assignee: Arthrex, Inc., Naples, FL (US)

( * ) Notice: Subject to any disclaimer, the term of this patent is extended or adjusted under 35 U.S.C. 154(b) by 826 days.

(21) Appl. No.: 12/941,554

(22) Filed: Nov. 8, 2010

(65) Prior Publication Data
US 2011/0118762 A1    May 19, 2011

Related U.S. Application Data

(60) Provisional application No. 61/261,604, filed on Nov. 16, 2009.

(51) Int. Cl.
*A61B 17/04* (2006.01)

(52) U.S. Cl.
CPC ......... *A61B 17/0401* (2013.01); *A61B 17/0485* (2013.01); *A61B 2017/0445* (2013.01)

(58) Field of Classification Search
CPC .................. A61B 17/0401; A61B 2017/0445; A61B 2017/0459; A61B 2017/0414
USPC ................................ 606/148, 232; 623/13.14
See application file for complete search history.

(56) References Cited

U.S. PATENT DOCUMENTS

| | | | |
|---|---|---|---|
| 5,176,691 A * | 1/1993 | Pierce | 606/148 |
| 5,466,241 A * | 11/1995 | Leroy et al. | 606/139 |
| 6,544,281 B2 | 4/2003 | ElAttrache et al. | |
| 7,329,272 B2 | 2/2008 | Burkhart et al. | |
| 2003/0004545 A1 * | 1/2003 | Burkhart et al. | 606/232 |
| 2005/0055052 A1 * | 3/2005 | Lombardo et al. | 606/232 |
| 2007/0219567 A1 * | 9/2007 | Bayer et al. | 606/148 |
| 2007/0225719 A1 * | 9/2007 | Stone et al. | 606/72 |
| 2008/0208253 A1 | 8/2008 | Dreyfuss et al. | |
| 2008/0275431 A1 * | 11/2008 | Stone et al. | 606/1 |

* cited by examiner

*Primary Examiner* — Alexander Orkin
(74) *Attorney, Agent, or Firm* — Dickstein Shapiro LLP

(57) ABSTRACT

Techniques and reconstruction systems for knotless tissue fixation using a driver with a cannulated interference device or fixation device preloaded on the shaft of the driver. An eyelet, adjustable in size, is formed of a loading suture provided at the distal end of the driver shaft. A working suture attached to the tissue to be fixed is passed through the eyelet. The size of the eyelet is adjusted by the user once the working suture is passed through the eyelet, to capture the working suture with the eyelet. The cannulated interference device is then advanced down the shaft to secure the working suture in a bone socket.

8 Claims, 7 Drawing Sheets

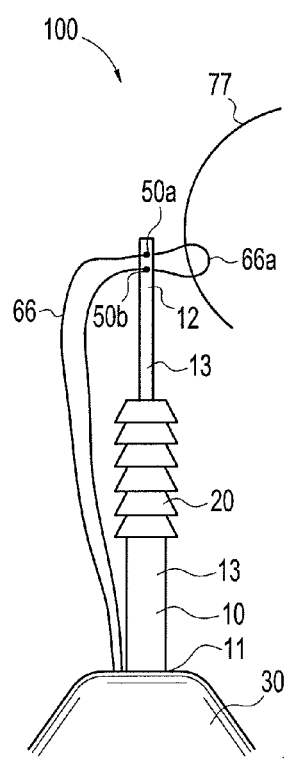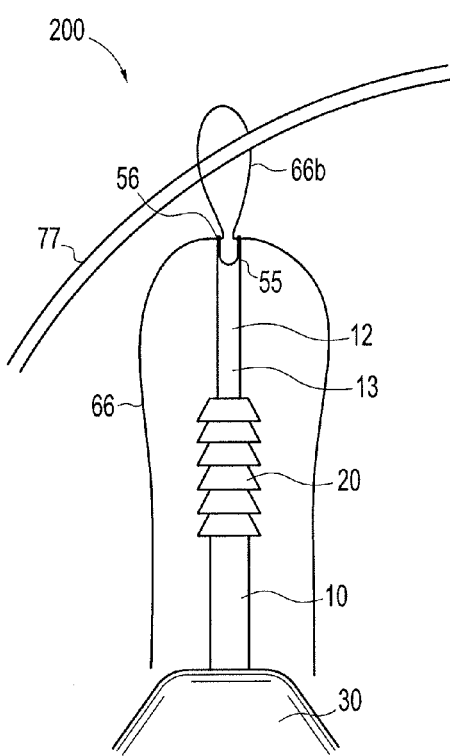

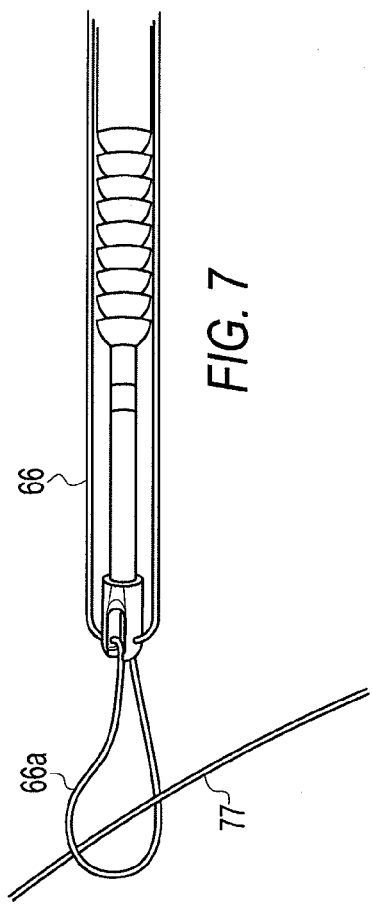
FIG. 7
FIG. 8
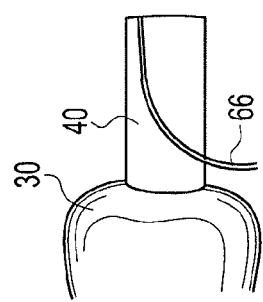
FIG. 9

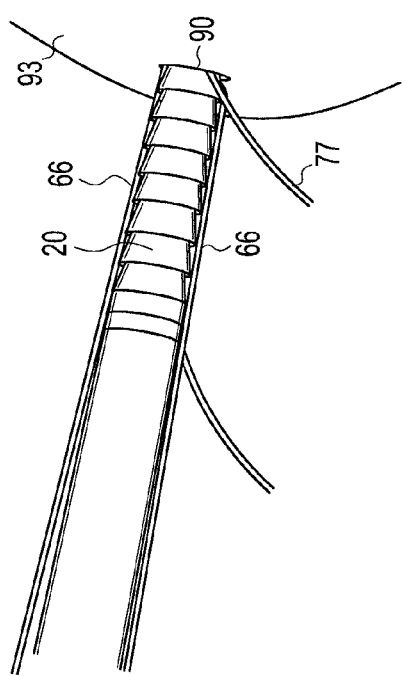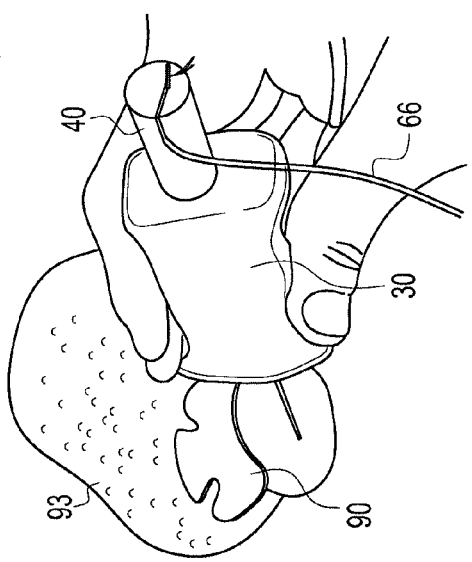

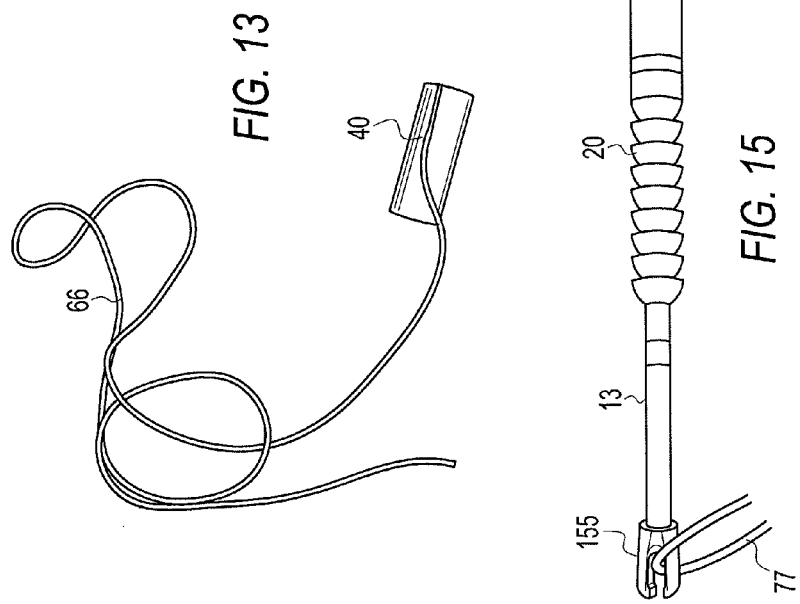
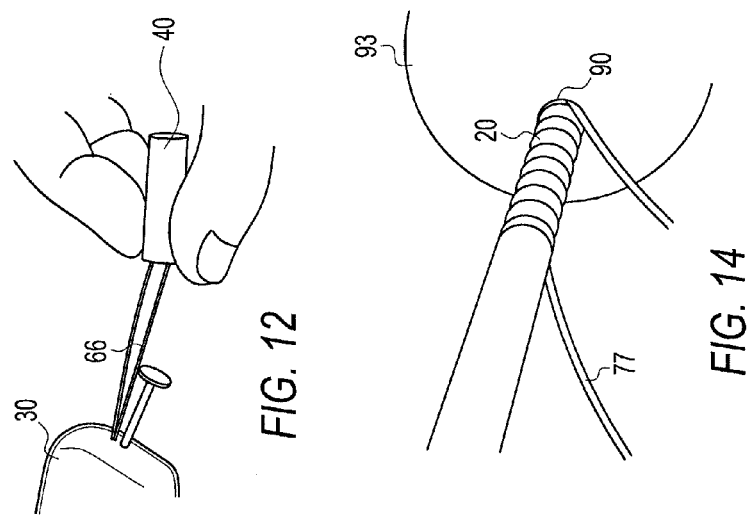

SUTURE ANCHOR EYELET WITH SUTURE LOADER

CROSS-REFERENCE TO RELATED APPLICATIONS

This application claims the benefit of U.S. Provisional Application No. 61/261,604, filed Nov. 16, 2009, the entire disclosure of which is incorporated by reference herein.

FIELD OF THE INVENTION

The present invention relates to surgical devices and, more particularly, to methods and devices for fixation of sutures and tissue to bone.

BACKGROUND OF THE INVENTION

Surgical techniques and associated devices for securing soft tissue to bone which allow free sliding of suture ends attached to soft tissue or graft (to ensure the positioning of the soft tissue or graft at an appropriate distance from the device) are known in the art. For example, a fixation device and associated surgical technique that allow precise advancement and guiding of a plug or screw into a blind hole or socket are disclosed in U.S. Pat. No. 7,329,272, the disclosure of which is incorporated by reference in its entirety herein.

As detailed in U.S. Pat. No. 7,329,272, and as shown in FIG. 1 of the present application, cannulated plug or screw 20 is pre-loaded onto a driver 10 provided with an eyelet implant 50 at its distal end. Suture 77 attached to the soft tissue or graft 70 is passed through an aperture 55 of the eyelet implant 70 located at the distal end of the driver 10. The distal end of the driver together with the eyelet implant is inserted into the bottom of the hole 90, with the screw or plug 20 disposed just outside the hole. Tension is applied to the suture to position the soft tissue or graft 70 at the desired location relative to the bone hole. The screw or plug 20 is then fully advanced into the pilot hole by tapping the interference screw or plug until the cannulated plug or screw securely engages and locks in the eyelet implant 50, so that the cannulated plug or screw 20 with the engaged eyelet implant 50 is flush with the bone.

The above-identified technique (the Arthrex PushLock™ technique) requires the user to load the suture (attached to the graft) through an aperture of the eyelet implant located at the distal end of the driver. This aperture is typically a very small orifice or very small hole and, thus, threading of the suture through such small aperture is difficult to manage during surgery.

A novel eyelet design (with a larger suture eyelet) that allows the user to feed working sutures through the eyelet, with less difficulty, is needed.

SUMMARY OF THE INVENTION

The present invention provides devices, assemblies and methods for interference fixation of a suture (attached to tissue such as soft tissue, graft or tendon) in a bone socket or hole.

An exemplary knotless suture anchor assembly of the present invention includes an eyelet loop having an adjustable size and being removably attached to a driver shaft; a flexible strand attached to tissue and passed through the eyelet loop; and an interference device that is preloaded on the driver shaft and secures the flexible strand in a bone socket or hole. The eyelet loop may be formed by passing a flexible strand through apertures provided directly in the shaft or in a forked tip (which may be integral to the shaft or detachable from the shaft). The size of the eyelet loop is adjusted once the flexible strand is passed through the eyelet loop, to capture the flexible strand in the forked tip.

A method of knotless tissue fixation according to the present invention comprises inter alia the steps of: attaching a flexible strand to tissue to be fixated; capturing the flexible strand attached to tissue to be fixated by feeding the strand through an eyelet loop removably attached to a driver shaft; inserting the flexible strand into a bone socket; and advancing an interference device toward the flexible strand and into the bone socket, to secure the flexible strand into the bone socket.

These and other features and advantages of the invention will be more apparent from the following detailed description that is provided in connection with the accompanying drawings and illustrated exemplary embodiments of the invention.

BRIEF DESCRIPTION OF THE DRAWINGS

FIG. 2 illustrates a tipless knotless suture anchor assembly according to a first embodiment of the present invention, with a first strand (loading suture) forming an eyelet loop (which is removed once working sutures are at the bottom of the bone socket) and with one second strand (one working suture) fed through the hole in the eyelet loop.

FIG. 3 illustrates a second embodiment of a tipless knotless suture anchor assembly with a forked tip of the present invention, with a first strand (loading suture) forming an eyelet loop and with two second strands (two working sutures) fed through the hole in the suture eyelet loop.

FIG. 4(a) illustrates a perspective view of the detachable anchor tip of the anchor assembly of FIG. 4.

FIG. 4(b) illustrates another perspective view of the detachable anchor tip (implant tip) of FIG. 4(a), rotated about 90 degrees.

FIG. 4(c) illustrates another perspective view of the detachable anchor tip (implant tip) of FIG. 4(b).

FIG. 7 illustrates another view of the suture anchor assembly of FIG. 4 and with a second strand (working suture) fed through the extended eyelet loop formed from the first strand (loading suture).

FIG. 8 illustrates the suture anchor of FIG. 7, with the free end of the first strand (loading suture) pulled tightly and with the second strand (working suture) loaded into the eyelet loop.

FIG. 9 illustrates a view of a most proximal end of the handle of the driver of FIG. 7, with the end of first strand (loading suture) cleated into the slot on the cap to hold secure.

FIG. 10 illustrates the suture anchor assembly of FIG. 8 with the second strand (working suture) and the interference device inserted into a bone hole.

FIG. 11 illustrates another view of the suture anchor assembly of FIG. 10 but from the proximal end of the handle and the cap.

FIG. 12 illustrates the suture anchor assembly of FIG. 11 with the cap pulled off and with the free one end of the first strand (loading suture) un-cleated.

FIG. 13 illustrates the cap of FIG. 12 with the first strand (loading suture) connected to it.

FIG. 14 illustrates the suture anchor assembly of FIG. 11 inserted into a hole with the first strand (loading suture) removed and the second strand (working suture) captured in the hole.

FIG. 15 illustrates another view of the suture anchor assembly of FIG. 8 without showing the bone to illustrate how the working suture is captured within the tip due to tension on the working suture.

DETAILED DESCRIPTION OF THE PREFERRED EMBODIMENTS

Figure 1:
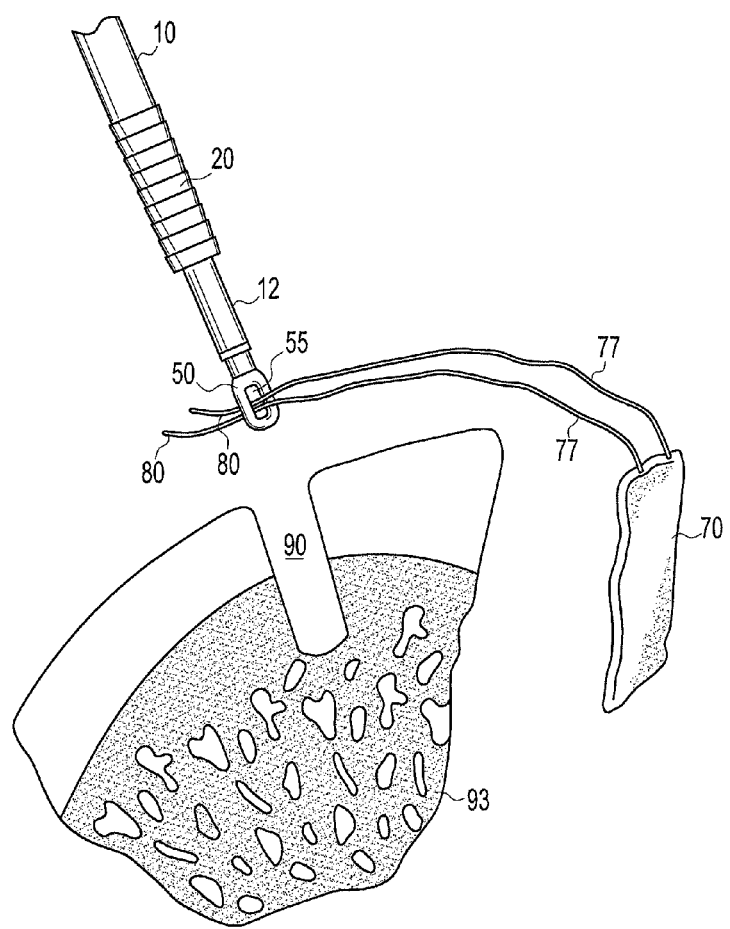
FIG. 1 illustrates a knotless suture anchor assembly as disclosed in U.S. Pat. No. 7,329,272, with suture connected to tissue passing through the eyelet of the anchor.

The present invention provides devices, assemblies and methods for interference fixation of a suture (attached to tissue such as soft tissue, graft or tendon) in a bone socket or hole.

An exemplary knotless suture anchor assembly of the present invention includes an eyelet loop having an adjustable size and being removably attached to a driver shaft; a flexible strand attached to tissue and passed through the eyelet loop; and an interference device that is preloaded on the driver shaft and secures the flexible strand in a bone socket or hole. The eyelet loop may be formed by passing a flexible strand through apertures provided directly through the shaft or in a forked tip (which may be integral to the shaft or detachable from the shaft). The size of the eyelet loop may be adjusted (for example, increased to allow the flexible strand to be passed through the eyelet loop, or decreased to capture the flexible strand in the forked tip).

An exemplary knotless device of the present invention comprises a threaded anchor body; an anchor tip with an eyelet loop having an adjustable size and being removably attached to the anchor tip, the anchor tip being engageable with the anchor body; and a flexible strand that is attached to tissue to be fixated and that is passed through the eyelet loop.

An exemplary knotless suture anchor assembly of the present invention comprises a driver with a shaft having a proximal end and a distal end; a cannulated interference device or fixation device preloaded on the driver and disposed coaxially with the shaft; an eyelet loop formed by a first strand (a loading suture) at the distal end of the shaft, the eyelet loop having an adjustable size and being removably attached to the shaft; and a second strand (a working suture) passed through the eyelet loop and attached to soft tissue, graft or tendon. The size of the eyelet loop is adjusted by the user once the second strand is passed through the eyelet loop, to capture the second strand with the eyelet loop. The cannulated device secures the captured strand in a bone socket or hole.

In an exemplary embodiment, the eyelet loop is formed by providing at least two apertures at the end of the driver shaft (and directly into the shaft) and passing the first strand (loading suture) through the apertures, to form the eyelet loop. According to another exemplary embodiment, the eyelet loop is formed by preloading a first strand (loading suture) through lateral through-holes provided within opposing arms of a forked tip at a most distal end of the shaft (a rigid eyelet design). According to yet another embodiment, the eyelet loop is formed by providing an anchor tip (implant tip) detachable from the shaft, and preloading a first strand (loading suture) through lateral through-holes provided within opposing arms of the detachable anchor tip. Once passed through the holes in the shaft or forked tip, the strand between the holes or the two forked tips is extended into a larger loop, creating a large eyelet loop.

In use, the user feeds at least one second strand (working suture) through the large eyelet loop formed by the first, loading suture. Once the second strands are loaded, the user tightens the first suture which reduces the size of the eyelet loop, and forces the second strands (working sutures) into the rigid forked tip eyelet. The first, loading suture is held securely to the suture anchor driver during insertion, to keep the second strands (working sutures) secure within the forked tip eyelet. The first strand (loading suture) is removed once the second strands (working sutures) are secured within a bone socket.

In an exemplary embodiment only, the present invention provides an eyelet implant with a rigid eyelet design provided with a forked tip (implant tip) with a lateral through-hole extending from tip to tip. A loading (stay) suture is preloaded through the hole. The loading suture between the two forked tips is extended into a larger loop which creates a larger suture eyelet. The user feeds the working sutures through this large suture eyelet (formed by the loading suture). Once the working sutures are loaded, the user tightens the loading suture which reduces the size of the suture eyelet, and forces the working sutures into the rigid forked tip eyelet. The loading suture is held securely to the suture anchor driver during insertion, to keep the working sutures secure within the forked tip eyelet. The working suture is attached to tissue to be secured or fixated (for example, soft tissue, graft or tendon) and inserted into a bone socket or hole after which is secured therein with a fixation device (for example, an interference device such as a plug or a threaded anchor body). The loading suture is removable (i.e., it may be removed from the driver at the end of the insertion and fixation process, when the working suture is securely captured and seated within the bone socket). Alternatively, the loading suture may be tied around the working suture and the ends of it cut short.

A method of knotless tissue fixation according to the present invention comprises inter alia the steps of: attaching a flexible strand to tissue to be fixated; capturing the flexible strand attached to tissue to be fixated by feeding the strand through an eyelet loop removably attached to a driver shaft; inserting the flexible strand into a bone socket; and advancing an interference device toward the flexible strand and into the bone socket, to secure the flexible strand into the bone socket.

A method of soft tissue repair according to the present invention comprises inter alia the steps of: providing a hole in a bone at a location at which a soft tissue graft is to be affixed; attaching at least one suture to the soft tissue graft to be affixed; preloading a cannulated interference device on a shaft of a driver; capturing the suture attached to the graft by feeding the suture through an eyelet loop removably attached to a distal end of the shaft; inserting the suture into the hole by inserting the distal end of the driver into the hole; pulling on one end of the suture to draw the suture through the eyelet loop such that the soft tissue graft attached to the suture is drawn toward the hole; and inserting the interference device into the hole so that the cannulated interference device is advanced toward the suture, to secure the suture in the hole.

Referring now to the drawings, where like elements are designated by like reference numerals, FIGS. 2-15 illustrate exemplary embodiments of knotless suture anchor assembly 100, 200, 300 with eyelet loop 66a, 66b, 66c (suture loader 66a, 66b, 66c) of the present invention that may be used in conjunction with a driver 10 preloaded with an interference device (fixation device) 20. Preferably, the interference device 20 is a plug, which may be formed of a polymer such as PEEK, a bioabsorbable material such as PLLA, or a metal. The plug is provided with rounded annular ribs separated by rounded annular grooves. The outer diameter of the rounded ribs and grooves is substantially constant. The plug may taper towards the distal end. The plug also contains a cannula, preferably hex-shaped, for accommodating the inner correspondingly shaped shaft of the driver.

A first embodiment of the invention is shown in FIG. 2, in which eyelet loop 66a of knotless suture anchor assembly 100 is formed by threading a first strand (a loading suture) 66 through apertures 50a, 50b at a most distal end 12 of shaft 13 of driver 10. The loop 66a of the first strand (loading suture) 66 effectively provides an enlarged eyelet loop 66a as compared to the eyelet 55 of the suture anchor of FIG. 1.

As also shown in FIG. 2, a second strand (working suture) 77 is fed through the eyelet loop 66a formed by the first strand (loading suture) 66. The second strand (working suture) 77 is attached to tissue to be fixated (for example, soft tissue, graft or tendon). Eyelet loop 66a has an adjustable size and is removably attached to the shaft 13. Once the second strand 77 is passed through the eyelet loop 66a, the size of the eyelet is adjusted by the user so that the second strand 77 is securely captured within the decreased-size eyelet. In an exemplary and illustrative embodiment only, the first strand (loading suture) 66 is a #1-0 FiberWire® suture, manufactured by Arthrex Inc, of Naples, Fla., and the second strand (working suture) 77 is a #2 FiberWire® suture.

The first and second strands may be formed of similar or different materials and may have cross-sections of various forms and geometries, including round, oval, rectangular, or flat, among others, or combination of such forms and geometries. In an exemplary embodiment only, at least one of the first and second strands 66, 77 may be provided as a suture tape or as a round suture, or as a combination of tape and round suture. The diameter of first and second strands 66, 77 may be constant or may vary.

In an exemplary embodiment, at least one of first and second strands 66, 77 may contain strands of a high strength suture material, such as Arthrex FiberWire® suture disclosed in U.S. Pat. No. 6,716,234, incorporated herein by reference, with optional colored strands to assist surgeons in distinguishing between suture lengths. If desired, at least one of the first and second strands 66, 77 may comprise a biological material (for example, collagen, collagen strands, a bioabsorbable polymer such as collagen-based material, or an extracellular matrix protein (such as fibronectin, elastin or laminin, among others). The first and second strands 66, 77 may be suture strands that may be coated, impregnated, or otherwise stiffened with a material such as plastic, for example.

A method of a graft fixation technique employing the knotless suture anchor assembly 100 of FIG. 2 proceeds by first securing soft tissue, graft, or tendon (for example, a biceps tendon or a rotator cuff) to working suture 77. At least one suture 77 is passed though the graft at desired points. The graft and suture 77 will be secured within a pilot hole or socket 90 formed in the bone or cartilage 93 (FIG. 10) using a drill or punch, at the location where the tissue is to be secured. Next, working suture 77 is passed through eyelet loop 66a of assembly 100. Eyelet loop 66a is formed by preloading the first strand (a loading suture) 66 through apertures 50a, 50b provided directly into the shaft 13 of driver 10. The length (suture) of the first strand 66 extending between the two apertures 50a, 50b is extended into a larger loop which creates a larger eyelet loop 66a (with perimeter and surface area larger than those of the eyelet 55 of the suture anchor of FIG. 1). The second strand (working suture) 77 is passed through the enlarged eyelet loop 66a.

The size of the eyelet is then adjusted (i.e., decreased) by pulling free ends of first strand (loading suture) 66. The second strand (working suture) 77 is securely captured within the decreased-size eyelet. The driver 10 is positioned so that the eyelet loop 66a and the working suture 77 at the distal end 12 is held at the bottom of the hole 90, keeping the interference device 20 just outside the pilot hole 90. Tension is then applied to the loading suture 66 and working suture 77 freely slides through the aperture created by eyelet loop 66a, allowing the graft 70 to be positioned close to the edge of the pilot hole 90. Once tensioning of the suture 66 has been completed, the interference device 20 is then impacted into the pilot hole 90 so that the interference device 20 advances toward the distal end 12 of driver 10 and securely engages and locks in the working suture 77. After the interference device 20 is fully inserted, the driver is removed and the ends of the first suture 66 can be removed by clipping them short, or the first strand 66 can be removed entirely, leaving the graft securely fastened to bone 93.

FIG. 3 illustrates a second embodiment of the invention, according to which knotless suture anchor assembly 200 includes an eyelet loop 66b preloaded through a forked tip 55 of the distal end 12 of driver 10 and integral to the shaft 13 of driver 10. Forked tip 55 may have a generally horseshoe-shaped configuration (with an open distal end) or may be a forked end with at least one through-hole or aperture 50a, 50b on each arm 56 of the forked end 55 to allow a first strand 66 to pass thereto and to form suture eyelet loop 66b.

Loading suture 66 is threaded through the apertures 50a, 50b on the arms 56 of the forked tip 55, as shown in FIG. 3. At least one second strand (working suture) 77 is passed through the eyelet loop 66b. FIG. 3 illustrates an exemplary embodiment with two working sutures 77 fed through the eyelet loop 66b formed by the loading suture 66. As in the previously-described embodiment, the suture of the first strand 66 extending between the two apertures 50a, 50b is extended into a larger loop which creates a larger eyelet loop 66b (with a perimeter and surface area larger than those of the eyelet 55 of the suture anchor of FIG. 1). The second strand (working suture) 77 is passed through this enlarged eyelet loop 66b.

A method of tissue fixation technique employing the knotless suture anchor assembly 200 of FIG. 3 proceeds by steps similar to those described above with reference to tissue fixation with knotless suture anchor assembly 100 and eyelet loop 66a, except that as the size of eyelet loop 66b is decreased, the two working sutures 77 are forced within aperture 55a of the forked tip 55.

FIGS. 4-15 illustrate details of a knotless suture anchor assembly 300 according to a third embodiment of the present invention, and exemplary steps of a tissue fixation with the knotless suture anchor assembly 300.

Figure 4:
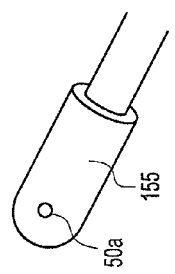
FIG. 4 illustrates a side view of a third embodiment of a knotless suture anchor assembly with a detachable anchor tip or implant tip (detachable forked tip) of the present invention, and with a first strand (loading suture) forming an eyelet loop.
Figure 4:
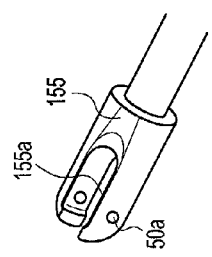
Figure 4:
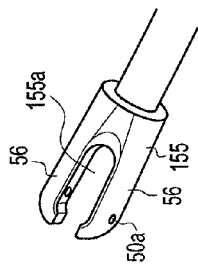
Figure 4:
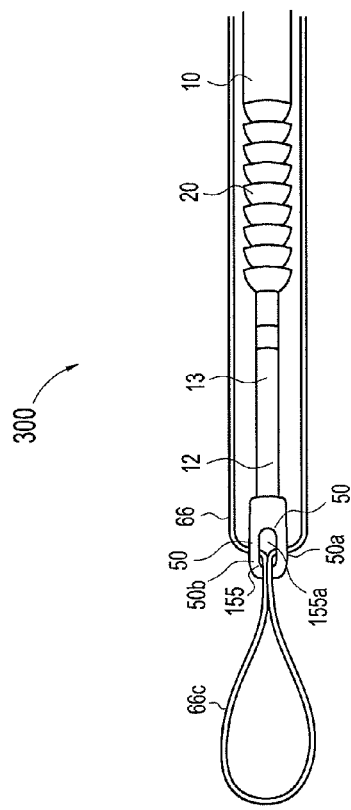

As illustrated in FIGS. 4-4c, knotless suture anchor assembly 300 includes eyelet loop 66c removably attached to forked tip 155 (implant tip or implant 155) which in turn is releasably attached to the distal end 12 of shaft 13 of the driver 10. The forked tip 155 is formed of a polymer material such as PEEK, or may be formed of metal. Advantageously, the forked tip 155 is made of a material similar to that of the interference device 20.

The forked tip of FIGS. 4-4c is releasably attached to the shaft 13 of the driver 10 and is provided with lateral through-holes 50a, 50b extending from tip to tip for receiving a stay or loading suture 66 (first strand 66). Loading suture 66 forms an eyelet loop 66c, as shown in FIG. 4. Eyelet loop 66c of loading suture 66 allows a second suture 77 (a working suture 77 attached to tissue or a graft) to more easily pass through the eyelet loop 66c formed by loading suture 66, as described in more detail below. Loading suture 66 is removed once working sutures 77 are at the bottom of the bone socket. In an exemplary and illustrative embodiment only, the first strand (loading suture) 66 is a #1-0 FiberWire® suture, manufactured by Arthrex Inc, of Naples, Fla., and the second strand (working suture) 77 is a #2 FiberWire® suture.

FIGS. 4(a)-(c) illustrate various views of the forked tip (implant) 155 of the present invention. Forked tip (implant) 155 is provided with one through-hole or aperture 50a, 50b on each arm 56 of the forked tip 155. Arms 56 define an aperture 155a which houses working sutures 77 when the size of the eyelet loop 66c is decreased (i.e., when the diameter of the loop becomes about zero and the strand 66 extends linearly from one aperture of one arm 56 to the other aperture of the other arm 56, in a direction about perpendicular to the longitudinal axis of the shaft 13).

Figure 6:
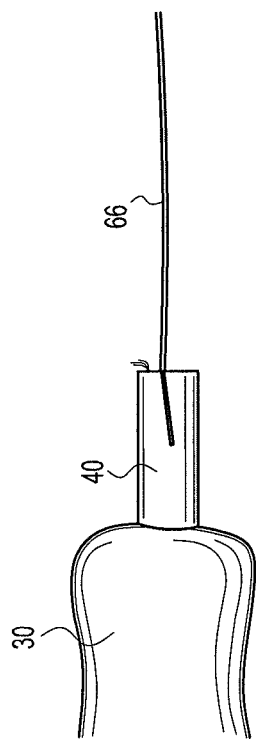
FIG. 6 illustrates an enlarged view of the cap of the handle of the assembly of FIG. 4 for installing the suture anchor of the present invention, showing one end of the first strand (loading suture) tied to the cap and the other end free to slide through the cap.
Figure 5:
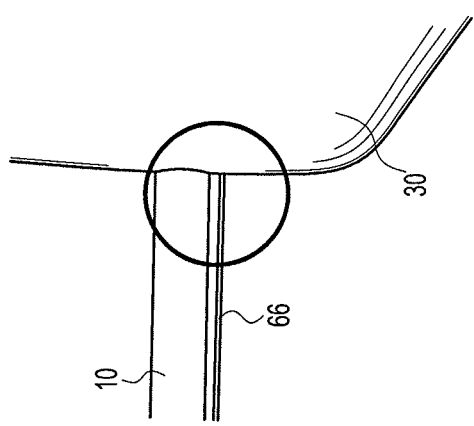
FIG. 5 illustrates an enlarged view of the most distal end of the handle of the assembly of FIG. 4 for installing the suture anchor of the present invention, showing the first strand (loading suture) fed up and through the handle, out of the other end.

FIG. 5 illustrates an enlarged view of the most distal end of handle 30 of the driver 10, showing the loading suture 66 (an exemplary #1-0 FiberWire suture) fed up and through the handle 30, out of the other end. FIG. 6 illustrates an enlarged view of a cap 40 of the driver 10, showing one end of the loading suture 66 tied to the cap 40, and with the other end free to slide through the cap 40.

A method of loading the working suture 77 through the eyelet loop 66c of the stay suture 66, and of subsequent soft tissue or graft fixation employing suture anchor assembly 300 of the present invention, is now described with reference to FIGS. 7-15. The present invention may be used to secure any type of soft tissue, graft, or tendon, such as, for example, a biceps tendon or a rotator cuff.

FIG. 7 illustrates a strand of working suture 77 (for example, a #2 FiberWire suture) fed through the extended eyelet loop 66c of the loading suture 66. The free end of the loading suture 66 is pulled tightly and the working suture 77 is loaded into the forked tip 155 (FIG. 8). The end of loading suture 66 is cleated into a slot on the cap 40 to hold it secure. Pulling on the ends of the loading suture 66 decreases the size of the eyelet loop 66c and forces the working suture 77 to enter aperture 155a of the forked tip 155 and be securely captured within the aperture, and bounded by the strand 66 (which extends linearly from one arm to the other arm of the forked tip 155, in a direction about perpendicular to the longitudinal axis of the shaft).

The driver 10 is positioned so that the eyelet implant 66c and the working suture 77 within aperture 155a is held at the bottom of the hole 90, keeping the interference device 20 just outside the pilot hole 90. Tension is then applied to the loading suture 66 and working suture 77 freely slides through the aperture 155a bounded by suture of the eyelet loop 66c, allowing the graft 70 to be positioned close to the edge of the pilot hole 90. Once tensioning of the suture 66 has been completed, the interference device 20 is then impacted into the pilot hole 90 so that the interference device 20 advances toward the distal end 12 of driver 10 and securely engages and locks in tip (implant) 155 with the working suture 77. After the interference device 20 is fully inserted, the driver is removed and the ends of the first suture 66 can be removed by clipping them short, or the first strand 66 can be removed entirely, leaving the graft securely fastened to bone 93.

FIGS. 10 and 11 illustrate the device inserted into hole or socket 90 until the anchor 20 is flush with the bone 93.

FIG. 12 illustrates cap 40 pulled off and with the free one end of loading suture 66 un-cleated. FIG. 13 illustrates the cap 40 with the loading suture 66 connected to it. FIG. 14 illustrates the interference device 20 inserted into hole 90 with loading suture 66 removed and working suture 77 captured within the hole 90.

FIG. 15 illustrates the device as implanted without showing the bone, illustrating the working suture 77 captured within the forked tip 155 due to the tension on the suture.

The suture 77 (attached to soft tissue or a graft) slides freely through the aperture 155a of the eyelet implant 155 and is held securely within the aperture by eyelet loop 66c, allowing the soft tissue or graft to be positioned close to the edge of the pilot hole. As described above, once tensioning of the suture 77 has been completed, the interference device 20 is impacted into the hole 90 so that the interference device 20 advances toward the distal end 12 of driver 10 and captures the working sutures 77 within the hole (abutting forked tip 155 which disengages shaft 13 of the driver 10). After the interference device 20 is fully inserted, the driver is removed and the ends of the working sutures can be removed by clipping them short, leaving the soft tissue or graft securely fastened to bone.

Although the present invention has been described in relation to particular embodiments thereof, many other variations and modifications and other uses will become apparent to those skilled in the art. Therefore, the present invention is to be limited not by the specific disclosure herein, but only by the appended claims.

What is claimed is:

1. A method of knotless tissue fixation, comprising the steps of:
    attaching a first flexible strand to tissue to be fixated;
    preloading a cannulated interference device on a driver shaft;
    forming an eyelet loop that is removably attached to the driver shaft by passing a second flexible strand through a plurality of lateral through-holes provided within opposing arms of a forked tip provided at a most distal end of the driver shaft and releasably attached to the driver shaft, wherein the cannulated interference device is disposed proximal to the forked tip on the driver shaft;
    passing the first flexible strand through the removably attached eyelet loop;
    subsequently, decreasing a size of the eyelet loop to force the first flexible strand into the forked tip and to secure the first flexible strand between the opposing arms of the forked tip; and
    securing the first flexible strand into a bone socket.

2. The method of claim 1, wherein the step of securing the first flexible strand between the opposing arms of the forked tip further comprises attaching one end of the second flexible strand to a removable cap located on the end of the driver shaft opposite the forked tip, and pulling on the ends of the second flexible strand.

3. The method of claim 1, wherein the step of securing the flexible strand into a bone socket further comprises the steps of inserting the first flexible strand into the bone socket by advancing the driver shaft into the bone socket; and advancing the interference device into the bone socket and towards the first flexible strand, to secure the first flexible strand within the bone socket.

4. A method of soft tissue repair, comprising the steps of:
    providing a hole in a bone at a location at which a soft tissue graft is to be affixed;
    attaching at least one suture to the soft tissue graft to be affixed;
    preloading a cannulated interference device on a shaft of a driver;

forming an eyelet loop that is removably attached to a distal end of the shaft by passing a flexible strand through a plurality of lateral through-holes formed on opposing arms of a forked tip that is releasably attached to the driver shaft, the eyelet loop having an adjustable perimeter, wherein the cannulated interference devices is disposed proximal to the forked tip on the driver shaft;

capturing the suture attached to the graft between the opposing arms of the forked tip by feeding the suture through the eyelet loop;

inserting the suture into the hole by inserting the distal end of the driver into the hole;

pulling on one end of the suture to draw the suture through the eyelet loop such that the soft tissue graft attached to the suture is drawn toward the hole; and inserting the interference device into the hole so that the cannulated interference device is advanced toward the suture, to secure the suture in the hole.

5. The method of claim 4, wherein the method further comprises the step of attaching one end of the flexible strand to a removable cap located on the end the shaft opposite the forked tip, and pulling on the ends of the flexible strand to adjust the perimeter of the loop, to capture the suture.

6. The method of claim 5, further comprising the step of removing the flexible strand, which further comprises removing the removable cap and detaching the end of the flexible strand from the removable cap.

7. The method of claim 4, further comprising the step of removing the flexible strand after the step of inserting the interference device into the hole.

8. The method of claim 4, wherein the soft tissue graft is drawn into the hole by pulling on the suture, and the interference device secures not only the suture but also the graft in the hole.

* * * * *